United States Patent
Rivolta et al.

(10) Patent No.: US 7,442,826 B2
(45) Date of Patent: Oct. 28, 2008

(54) PROCESS FOR THE PREPARATION OF NITROOXYDERIVATIVES OF PARACETAMOL

(75) Inventors: Romano Rivolta, Antibes (FR); Roberto Aureli, Bologna (IT)

(73) Assignee: Nicox S.A., Sophia Antipolis (FR)

( * ) Notice: Subject to any disclaimer, the term of this patent is extended or adjusted under 35 U.S.C. 154(b) by 28 days.

(21) Appl. No.: 10/579,904

(22) PCT Filed: Nov. 4, 2004

(86) PCT No.: PCT/EP2004/052806

§ 371 (c)(1), (2), (4) Date: May 19, 2006

(87) PCT Pub. No.: WO2005/054175

PCT Pub. Date: Jun. 16, 2005

(65) Prior Publication Data

US 2007/0149801 A1   Jun. 28, 2007

(30) Foreign Application Priority Data

Nov. 20, 2003  (EP) .................... 03292892

(51) Int. Cl.
*C07C 203/00* (2006.01)
*C07C 331/00* (2006.01)
*C07C 381/00* (2006.01)

(52) U.S. Cl. ..................................... 558/482

(58) Field of Classification Search ............ 558/482
See application file for complete search history.

(56) References Cited

U.S. PATENT DOCUMENTS 4,801,596 A    1/1989  Simon et al.
7,186,753 B1 *  3/2007  Del Soldato ............. 514/509

FOREIGN PATENT DOCUMENTS

WO    01/12584 A2    2/2001
WO    02/30866 A1    4/2002

* cited by examiner

*Primary Examiner*—Yvonne Eyler
*Assistant Examiner*—Jennifer Y Cho
(74) *Attorney, Agent, or Firm*—Arent Fox LLP

(57) ABSTRACT

The present invention relates to a new process for the preparation of a compound of the following formula (I):

9 Claims, No Drawings

PROCESS FOR THE PREPARATION OF NITROOXYDERIVATIVES OF PARACETAMOL

CROSS-REFERENCE TO RELATED APPLICATION

This application is a National Stage entry of International Application No. PCT/EP2004/1052806, filed Nov. 4, 2004. The disclosure of the prior application is hereby incorporated herein in its entirety by reference.

The present invention relates to a new process for the preparation of 4-(acetylamino)phenyl nitrooxyalkanoates, in particular of 4-(acetylamino)phenyl 4-nitrooxybutanoate. 4-(Acetylamino)phenyl 4-nitrooxybutanoate is a nitric oxide donating analgesic with significantly reduced liver toxicity in comparison with 4-(acetylamino)phenol (paracetamol or acetaminophen).

The preparation of 4-(acetylamino)phenyl 4-nitrooxybutanoate is described in the published International Patent Application WO 01/12584. The disclosed synthesis is reported in following Scheme 1. The product is obtained by condensation (esterification) of phenolic group of 4-(acetylamino)phenol with carboxylic group of 4-bromobutyric acid. The thus obtained 4-bromobutanoate is reacted with silver nitrate.

SCHEME 1

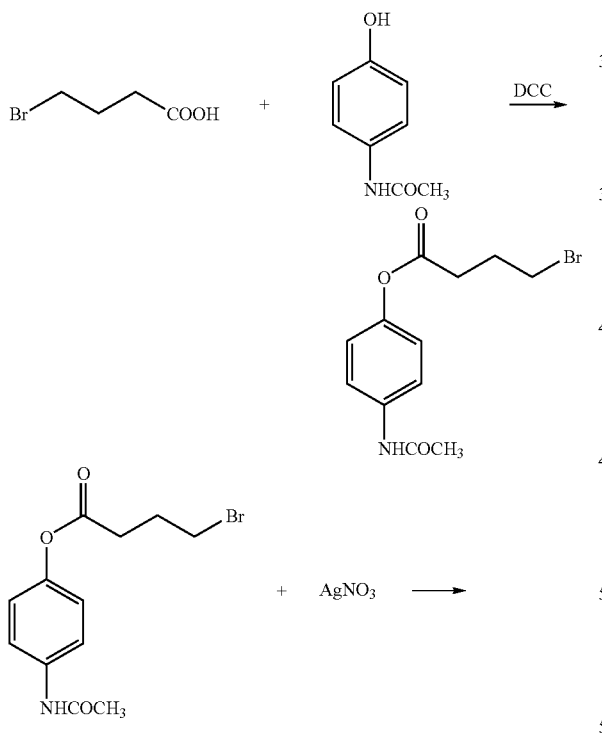

The principal drawbacks of the above reported synthesis are the use of the silver salts in an amount more than stoichiometric and the fact that 4-bromobutanoic acid is not commercially available. The use of the silver nitrate in a large amount makes the method expensive and not useful under the point of view of the industrial application. Furthermore the use of a transition metal in the last step of the process, makes difficult the complete removal of the same from the active pharmaceutical product, unless techniques of chromatographic purification are applied. Said techniques are not industrially applicable for the amount of drug necessary to satisfy the market demand of an analgesic drug. The present application provides a new method of synthesis which overcomes the drawbacks of the previous method.

The present invention relates to a process for preparing a compound of the following formula (I):

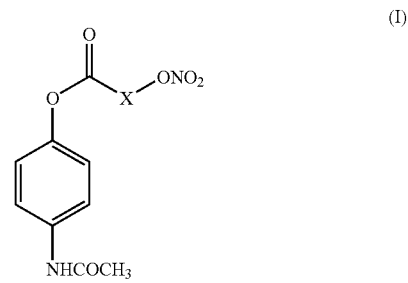

wherein X is a straight or branched $C_1$-$C_{20}$-alkylene chain, said process comprising reacting a compound of the following formula (II):

wherein M is a hydrogen atom or a cation of an alkaline or alkaline earth metal or an onium cation with a compound of the following formula (III):

$$O_2NO—X—COY \qquad (III)$$

wherein Y is OH, Cl, OCOOR, OCO—X—ONO$_2$, wherein R is a $C_1$-$C_6$ alkyl and X is as defined above.

X is preferably a straight or branched $C_1$-$C_6$ alkylene chain, more preferably X is an ethylene, propylene or butylene chain, most preferably it is propylene.

Y is preferably OH or Cl.

M is preferably a hydrogen atom, or a cation of Na or of K or tetralkylamonium or tetraalkylphosphonium.

When M is H and Y is OH, the reaction is carried out in the presence of a dehydrating agent in aprotic dipolar solvents such as THF, DMF, N-Methyl-pyrrolidone. The dehydrating agent is preferably dicyclohexylcarbodiimide (DCC); or DCC and an aminopyridine; Amberlyst-15; diethtyl azodicarboxylate and triphenylphosphine (Mitsunobu esterification reaction). Other dehydrating agents include chlorosilanes; methanesolsonyl chloride and triethylamine; and N,N-carbonyldiimidazole.

The molar ratio between the compound of formula (II) and the acid of formula (III) is from 0.5 to 2.0.

The reaction is carried out at a temperature ranging from 0° C. to 100° C.

When M is a cation of Na or K and Y is Cl, the reaction may be carried out in dipolar aprotic solvents such as tetrahydrofuran, dioxane, tert-butyl methylether, pyridine. When M is tetralkylamonium or tetralkylphosphonium and Y is Cl, the reaction is carried out in aprotic solvents such as toluene, chlorobenzene, tetrahydrofuran, tert-butyl methyl ether. The reaction may be carried out under phase transfer conditions. The reaction may be carried out at a temperature ranging from 0° C. to 100° C.

The molar ratio between the compound of formula (II) and the acid chloride of formula (III) is from 0.5 to 2.0.

One of the advantages of this new method in comparison to the known art is that of carrying out the process without employing silver salts which are expensive. The process of the invention instead uses cheap starting materials which are commercially available or can be easily obtained by commercially available compounds.

According to the present invention, compounds of formula (I) are obtained by a synthesis which does not involve chemical transformation of intermediates structurally related to the active principle. Therefore the formation of impurities structurally related to the end compounds of formula (I), which could make problematic the purification, is avoided. This is a further advantage in comparison with the process described in the prior art.

The synthetic results are surprising by considering the nature of the two reactants involved in the process: an oxidant, i.e. the molecule containing the nitrate group and a reductant, i.e. the compound containing the phenol group (phenols are used as antioxidants), which could have given rise to redox reactions.

Furthermore, it is also surprising that products deriving from the nucleophilic substitution of the nitrate group (a moderate leaving group) with the phenolic group (good nucleophile) are not obtained.

The compound of formula (II) wherein M is H is paracetamol, a commercially available compound.

The compounds of formula (II) wherein M is a cation of an alkaline metal or of an alkaline earth metals may be prepared by reacting 4-acetylaminophenol in a suitable organic solvent, for example tetrahydrofuran, dimethylformamide etc., with a base such as NaH, NaOH, KOtBu.

The compounds of formula (II) wherein M is a onium cation may be prepared by reacting 4-acetylaminophenol with tetralkylamonium or tetralkylphosphonium hydroxide or by reacting an alkaline salt of 4-acetylaminophenol with a tetralkylamonium or tetralkylphosphonium salt generally in a two phases system consisting of inorganic solvents such as toluene, chlorobenzene and water.

The compounds of formula (III), wherein Y is Cl, can be obtained from the corresponding compounds of formula (III) wherein Y is OH by procedures known to a person skilled in the art such as for example by treatment with $SOCl_2$/DMF cat., $PCl_5$ etc.

The compounds of formula (III) wherein Y is OCOOR can be obtained from the corresponding compounds of formula (III) wherein Y is OH by procedures known to a person skilled in the art such as for example by treating an alkaline metal salt of III with the ClCOOR of choice.

The compounds of formula (III) wherein Y is OCO—X—ONO2 can be obtained from the corresponding compounds of formula (III) wherein Y is OH by procedures known to a person skilled in the art such as for example by treatment with dehydrating agents.

The compound of formula (III) wherein Y is OH can be prepared transforming an acid of formula (IV)

$$HO—Y—COOH \quad\quad\quad (IV)$$

in the corresponding nitro derivative by reaction with sulfonitric mixture.

The preparation of the 4-nitrooxybutirric acid and the reaction with $PCl_5$ to give its corresponding acyl chloride is described in the patent U.S. Pat. No. 4,801,596 of Jan. 31, 1989. The nitration method consists in the addition of the sodium or potassium salt of the 4-hydroxybutirric acid, obtained by opening the γ-butyrolactone with KOH, to a sulfonitric mixture according to the following Scheme 2:

SCHEME 2

[Reaction scheme: γ-butyrolactone + KOH/MeOH → KOOC-(CH2)3-OH; then HNO3/H2SO4 in CH2Cl2 → HOOC-(CH2)3-ONO2]

EXAMPLES a) Synthesis of potassium 4-(hydroxy)butanoate

[Reaction scheme: γ-butyrolactone + KOH/MeOH → HO-(CH2)3-COO⁻K⁺]

A solution of gamma butyrolactone (2 g, 23.3 mmol) in methanol (5 ml) was added dropwise to a potassium hydroxide (1.28 g, 22.9 mmol) solution in methanol (10 ml) kept at 25° C. by external cooling.

The solution was kept at room temperature for 4 h 30'. The solvent was removed in vacuo until yellow solid residue. The solid was washed with $Et_2O$ and dried under reduced pressure.

The product was obtained as a yellowish solid (3.25 g).

Analyses: MS (ESI neg): 103 (M−) IR(KBr) cm$^{-1}$: 2958, 1653, 1562 (C=O), 1403, 1305, 1059.

b) Synthesis of 4-(nitrooxy)butanoic acid

[Reaction scheme: HO-(CH2)3-COO⁻K⁺ + HNO3/H2SO4 1:1 in CH2Cl2 → 2ONO-(CH2)3-COOH]

Nitric acid (100% $HNO_3$, 0.6 ml) was added dropwise to stirred sulphuric acid (96% $H_2SO_4$, 0.6 ml) kept at 0° C. by external cooling.

$CH_2Cl_2$ (10 ml) was added to the HNO3/H2SO4 mixture, and the resulting solution was stirred for 15 minutes. Potassium 4-(hydroxy)butanoate (500 mg, 3.52 mmol) was then added in small portions to the methylenechloride solution kept at 0-5° C. The mixture was kept under stirring for 6 hours while the temperature was allowed to reach 25° C. gradually. Water (50 ml) was added to the reaction mixture and the resulting mixture was extracted with $CH_2Cl_2$ (3×25 ml). The combined organic phases were washed with water, dried over $MgSO_4$ and concentrated to dryness under reduced pressure. 4-(Nitrooxy)butanoic acid was obtained as a yellow oil (300 mg, 57%) and used in the next step.

Analyses: TLC: (EtOAc/Petroleum ether 3/7) Rf=0.13 IR(oil) $cm^{-1}$: 3521 (—OH); 1770 (C=O); 1627, 1282 ($ONO_2$). $^1H$ NMR ($CDCl_3$, 300 MHz): 2.15-2.20 (2H, m, $CH_2$), 2.54 (2H, t, J=7.2 Hz, $CH_2$—COOH), 4.42 (2H, t, J=6.3 Hz, $CH_2$—$ONO_2$), 11.90 (1H, br s, COOH).

c) Synthesis of 4-(nitrooxy)butanoyl chloride

Thionyl chloride (0.6 ml, 7.7 mmol) was slowly added, under stirring and under argon, to a solution of 4-(Nitrooxy) butanoic acid (1.00 g, 6.7 mmol) in anhydrous $Et_2O$ (25 ml) kept 0° C. A few drops of DMF (4-5 drops) were also added under stirring to the reaction mixture and the reaction temperature was allowed to rise to r.t. (ca. 20° C.). The reaction mixture was stirred at room temperature and under argon for 5 hours. The reaction mixture was concentrated in vacuo to provide crude 4-(nitrooxy)butanoyl chloride.

Synthesis of 4-(acetylamino)phenyl 4-(nitrooxy)butanoate

Sodium hydride (270 mg of 60% NaH, 6.8 mmol) was added under argon and under magnetic stirring to a solution of 4-acetaminophenol (840 mg, 5.6 mmol) in dry THF (20 ml) kept at 0° C. The reaction mixture was stirred at 0° C. for 40 minutes. A solution of crude 4-(nitrooxy)butanoyl chloride in dry THF (10 ml), was then added dropwise to the reaction mixture kept at 0° C. The reaction temperature was allowed to rise to r.t. and the mixture was stirred for 18 hours. The unreacted 4-acetaminophenol was removed by washing the solution with 2M NaOH solution (75 ml). The resulting mixture was extracted with $CH_2Cl_2$ (3×75 ml). The combined organic phases were dried over $MgSO_4$ and concentrated under reduced pressure. Purification of the residue by silica gel column chromathography by using petroleum ether/ethyl acetate=30/70 mixture as eluent provided 300 mg (1.1 mmol, 40% yield on converted paracetamol) of pure 4-(acetylamino) phenyl 4-(nitrooxy)butanoate.

IR and LC-MS ESI-spectra of the product were identical to those of an authentic sample.

What is claimed is:

1. A process for preparing a compound of the following formula (I):

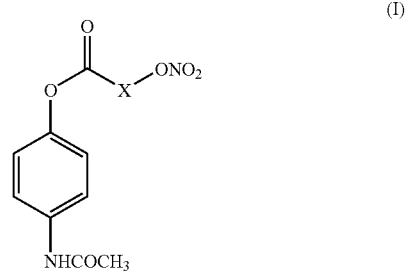

wherein X is a straight or branched $C_1$-$C_{20}$-alkylene chain, said process comprising reacting a compound of the following formula (II):

wherein M is a hydrogen atom or a cation of an alkaline or alkaline earth metal, an onium cation with a compound of the following formula (III):

$O_2NO$—X—COY (III)

wherein Y is OH, Cl, OCOOR, —OCO—X—$ONO_2$ wherein R is a $C_1$-$C_6$alkyl and X is as defined above.

2. The process according to claim 1 wherein X is a straight or branched $C_1$-$C_6$ alkyl chain.

3. The process according to claim 1 wherein X is a propylene chain.

4. The process according to claim 1 wherein Y is OH and M a hydrogen atom.

5. The process according to claim 4 wherein the reaction is carried out in aprotic dipolar solvents, in the presence of a dehydrating agent selected from: dicyclohexylcarbodiimide (DCC); or DCC and an aminopyridine; Amberlyst-15; diethyl azodicarboxylate and triphenylphosphine.

6. The process according to claim 1 wherein M is Na or K and Y is Cl.

7. The process according to claim 6 wherein the reaction is carried out in dipolar aprotic solvents selected from tetrahydrofuran, dioxane, tert-butyl methyl ether.

8. The process according to claims 1 wherein M is an onium cation and Y is Cl.

9. The process according to claim 8 wherein the onium cation is selected from tetraalkylammonium or tetraalkylphosphonium and the reaction is carried out in aprotic solvents selected from toluene, chlorobenzene, tetrahydrofuran, tert-butyl methyl ether.

* * * * *